(12) United States Patent
Hyde et al.

(10) Patent No.: US 8,463,391 B2
(45) Date of Patent: *Jun. 11, 2013

(54) SYSTEMS CONFIGURED TO DELIVER ENERGY OUT OF A LIVING SUBJECT, AND RELATED APPARTUSES AND METHODS

(75) Inventors: Roderick A. Hyde, Redmond, WA (US); Muriel Y. Ishikawa, Livermore, CA (US); Jordin T. Kare, Seattle, WA (US); Dennis J. Rivet, Portsmouth, VA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 803 days.

This patent is subject to a terminal disclaimer.

(21) Appl. No.: 12/456,846

(22) Filed: Jun. 23, 2009

(65) Prior Publication Data
US 2010/0065097 A1    Mar. 18, 2010

Related U.S. Application Data

(63) Continuation-in-part of application No. 12/378,152, filed on Feb. 11, 2009, now Pat. No. 8,295,941, and a continuation-in-part of application No. 12/316,811, filed on Dec. 15, 2008, now Pat. No. 8,280,520, and a continuation-in-part of application No. 12/283,911, filed on Sep. 15, 2008, now Pat. No. 8,340,777.

(51) Int. Cl.
*A61N 1/00* (2006.01)

(52) U.S. Cl.
USPC ............................................. 607/60; 607/61

(58) Field of Classification Search
USPC ....................................................... 607/60, 61
See application file for complete search history.

(56) References Cited

U.S. PATENT DOCUMENTS

| | | | |
|---|---|---|---|
| 5,320,098 A | 6/1994 | Davidson | |
| 5,387,259 A * | 2/1995 | Davidson | 600/310 |
| 5,835,457 A | 11/1998 | Nakajima | |
| 5,889,735 A | 3/1999 | Kawata et al. | |
| 5,897,330 A | 4/1999 | Watanabe et al. | |
| 6,898,464 B2 | 5/2005 | Edell et al. | |
| 2006/0139000 A1 * | 6/2006 | Bailey et al. | 320/114 |
| 2007/0027505 A1 | 2/2007 | Ginggen | |
| 2008/0097545 A1 | 4/2008 | Propato | |
| 2009/0171404 A1 * | 7/2009 | Irani et al. | 607/2 |

OTHER PUBLICATIONS

Roderick A. Hyde et al., U.S. Appl. No. 12/283,911, filed Sep. 15, 2008, "Systems Configured to Transmit Optical Power Signals Transdermally Out of a Living Subject, and Devices and Methods".
Roderick A. Hyde et al., U.S. Appl. No. 12/316,811, filed Dec. 15, 2008, "Systems Configured to Locate a Photonic Device Disposed in a Living Subject, and Related Apparatuses and Methods".
Roderick A. Hyde et al., U.S. Appl. No. 12/378,152, filed Feb. 11, 2009, "Systems Configured to Power At Least One Device Disposed in a Living Subject, and Related Apparatuses and Methods".
U.S. Appl. No. 13/604,005, filed Oct. 29, 2012, Hyde et al.
U.S. Appl. No. 13/603,904, filed Oct. 29, 2012, Hyde et al.
U.S. Appl. No. 13/603,859, filed Oct. 29, 2012, Hyde et al.

* cited by examiner

*Primary Examiner* — Eric D. Bertram
(74) *Attorney, Agent, or Firm* — Workman Nydegger

(57) ABSTRACT

Embodiments disclosed herein are directed to systems configured to deliver energy out of a living subject to power at least one external device, and related apparatuses, and methods of use.

32 Claims, 7 Drawing Sheets

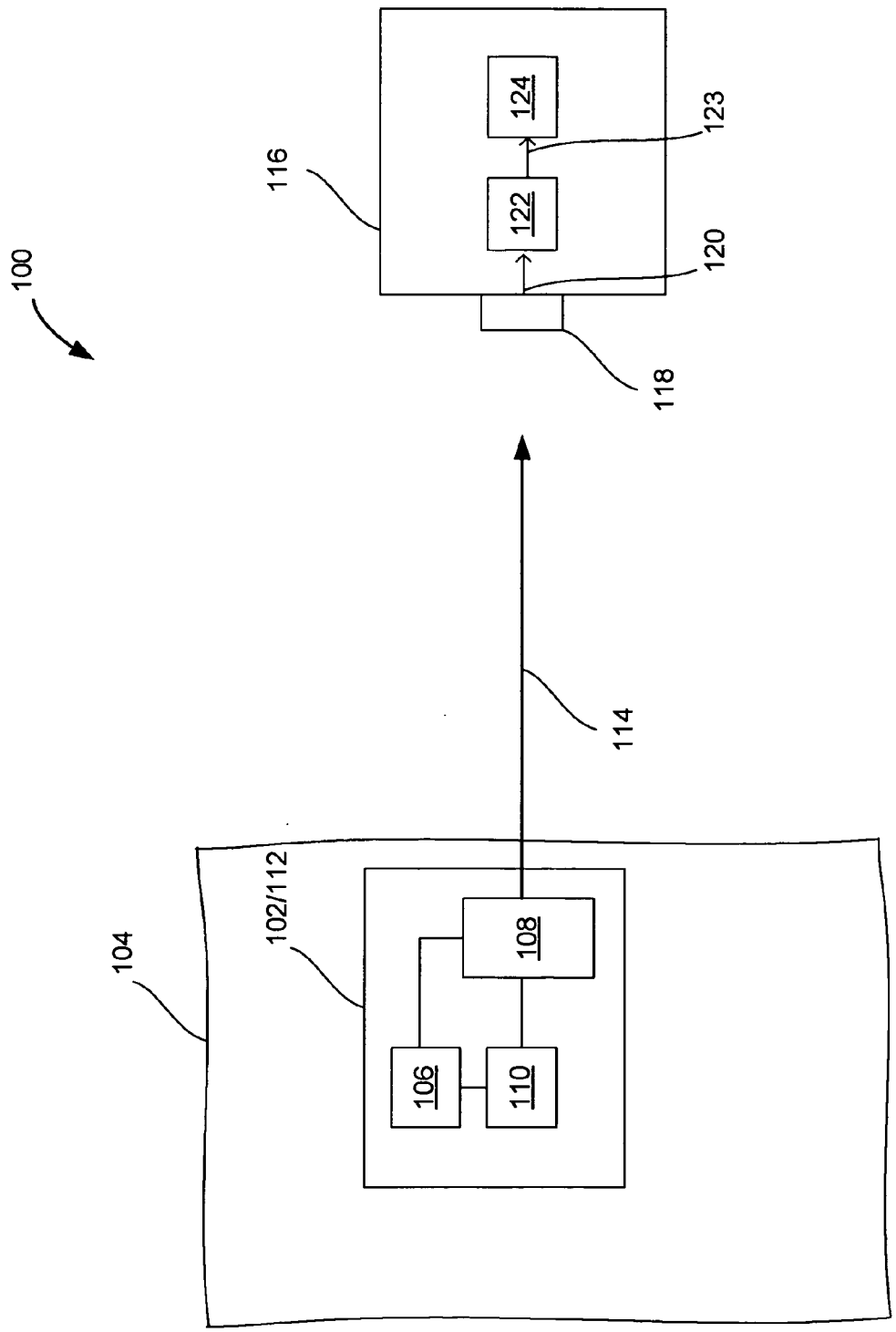

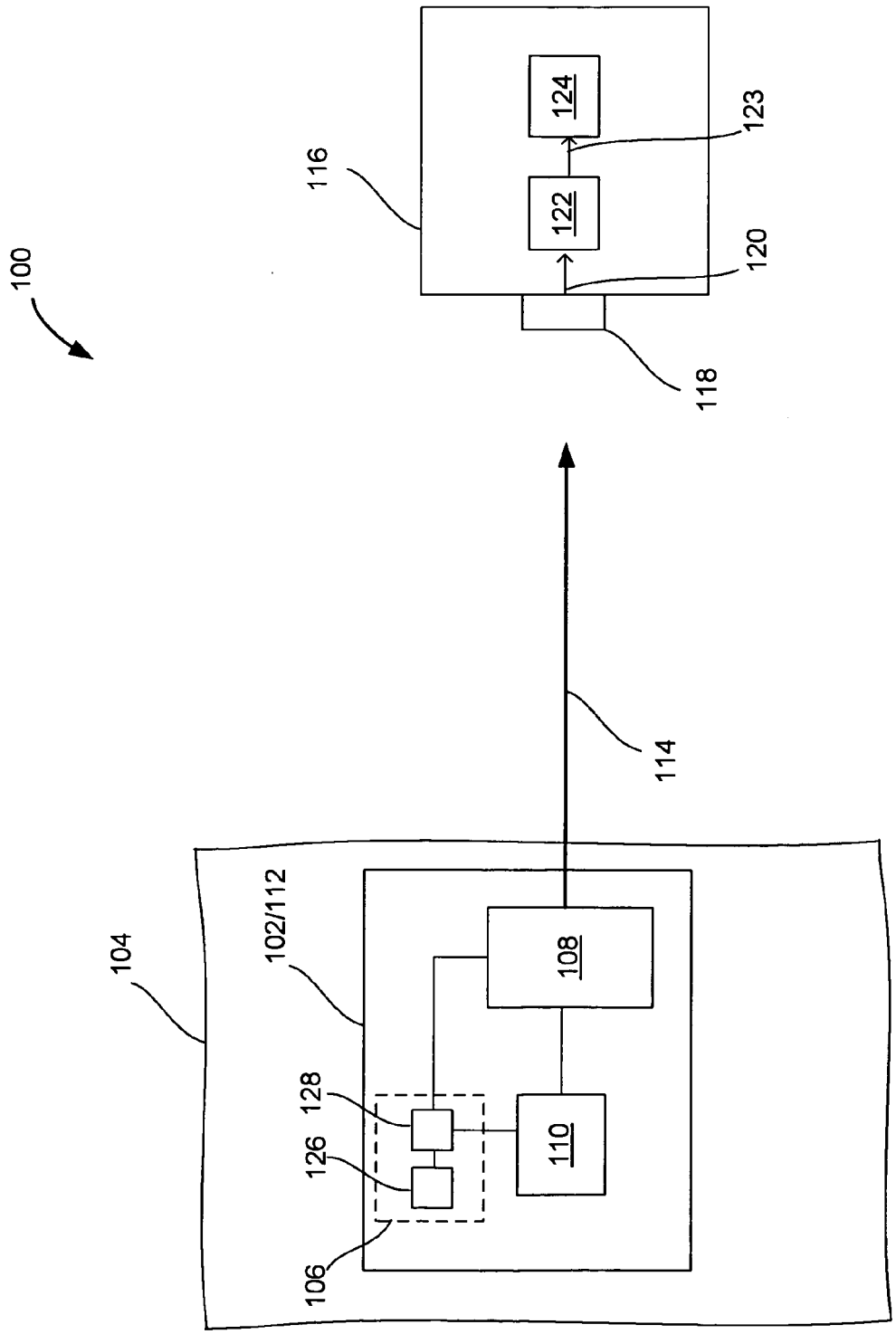

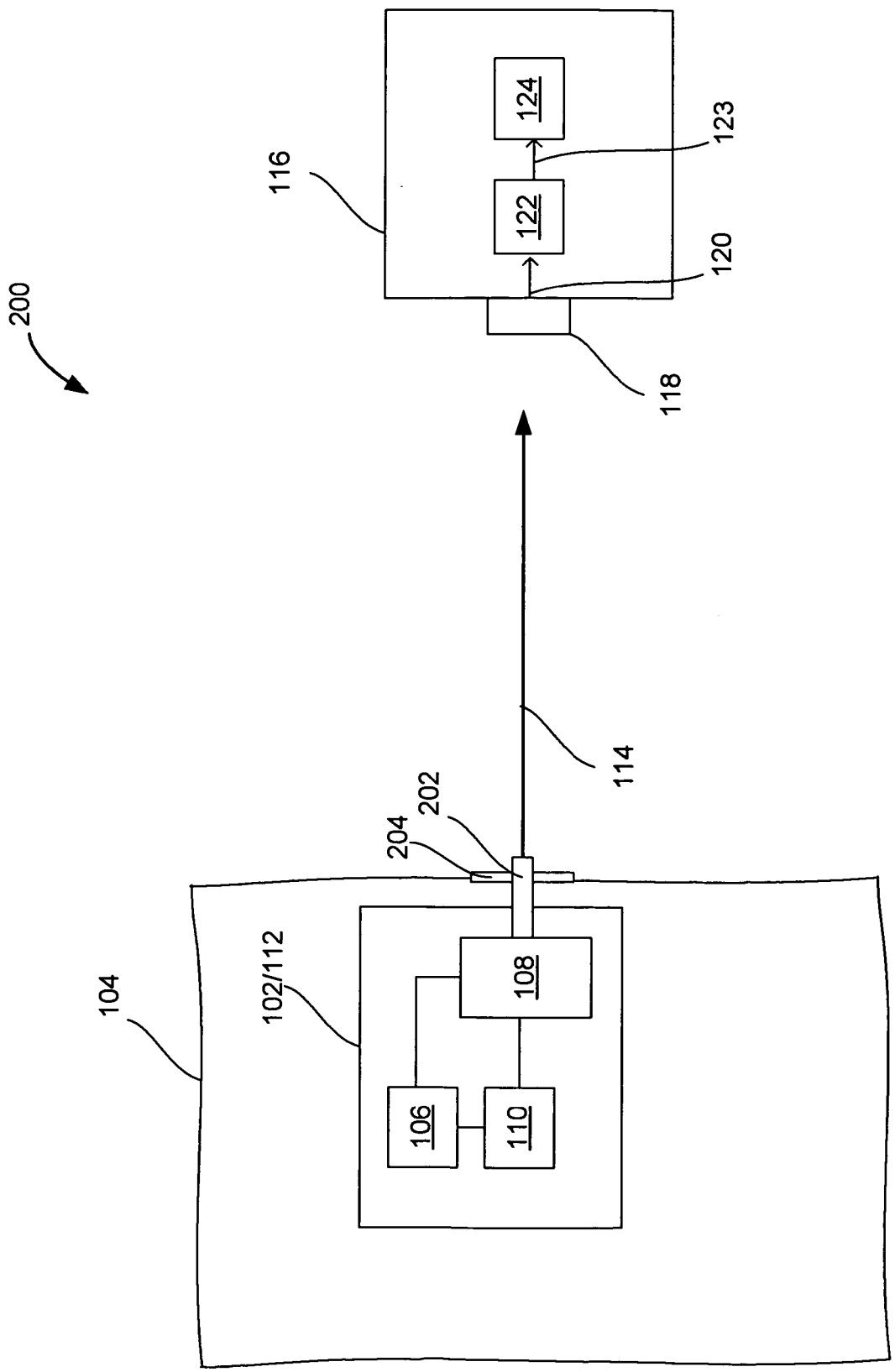

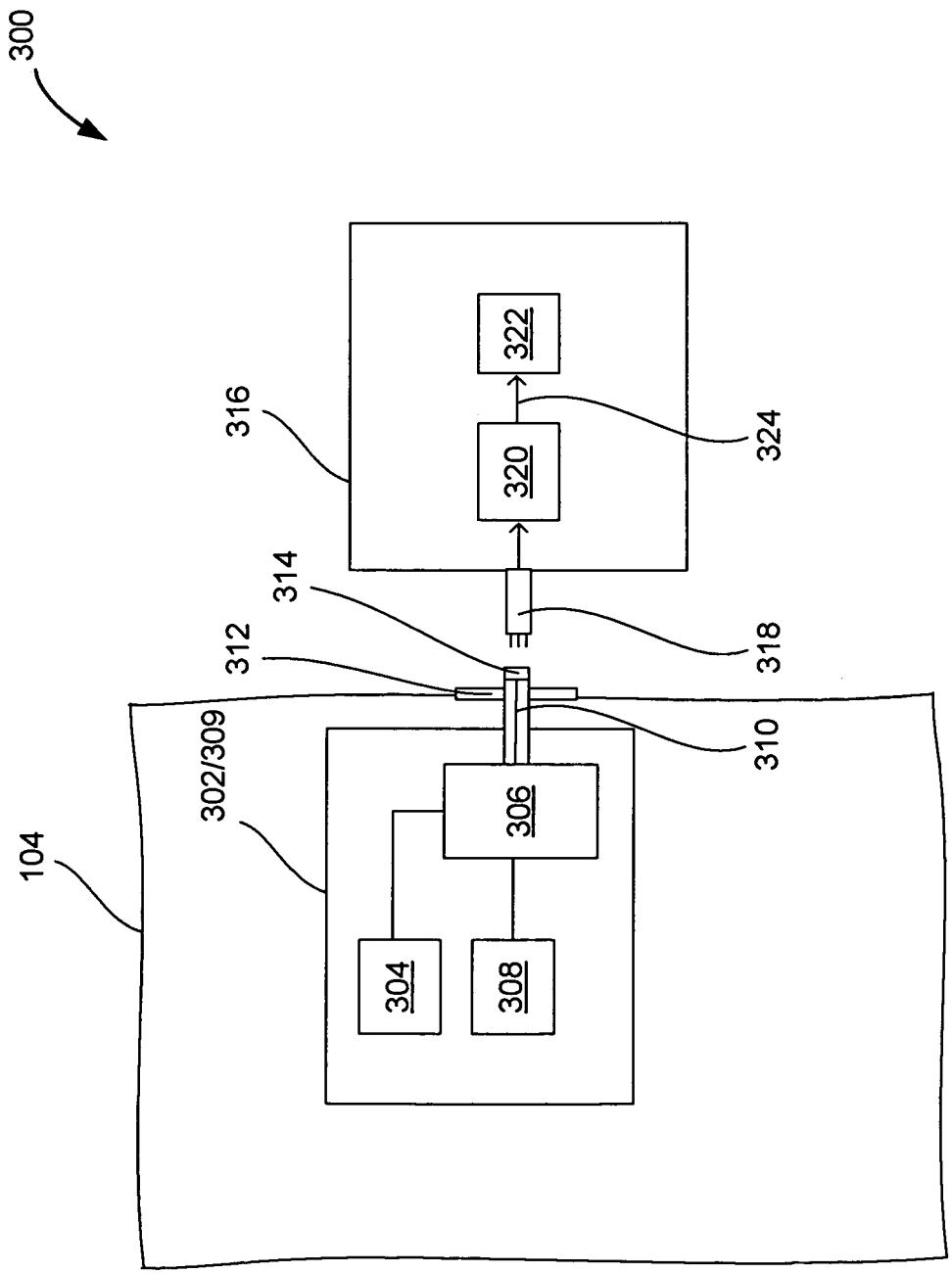

SYSTEMS CONFIGURED TO DELIVER ENERGY OUT OF A LIVING SUBJECT, AND RELATED APPARTUSES AND METHODS

RELATED APPLICATIONS

For purposes of the USPTO extra-statutory requirements, the present application constitutes a continuation-in-part of U.S. patent application Ser. No. 12/283,911, entitled SYSTEMS CONFIGURED TO TRANSMIT OPTICAL POWER SIGNALS TRANSDERMALLY OUT OF A LIVING SUBJECT, AND DEVICES AND METHODS, naming RODERICK A. HYDE, MURIEL Y. ISHIKAWA, DENNIS J. RIVET, ELIZABETH A. SWEENEY, LOWELL L. WOOD, JR., AND VICTORIA Y. H. WOOD as inventors, filed 15 Sep. 2008 now U.S. Pat. No. 8,340,777, or is an application of which a currently application is entitled to the benefit of the filing date.

For purposes of the USPTO extra-statutory requirements, the present application constitutes a continuation-in-part of U.S. patent application Ser. No. 12/316,811, entitled SYSTEMS CONFIGURED TO LOCATE A PHOTONIC DEVICE DISPOSED IN A LIVING SUBJECT, AND RELATED APPARATUSES AND METHODS, naming RODERICK A. HYDE, MURIEL Y. ISHIKAWA, DENNIS J. RIVET, LOWELL L. WOOD, JR., AND VICTORIA Y. H. WOOD as inventors, filed 15 Dec. 2008, now U.S. Pat. No. 8,280,520, or is an application of which a currently application is entitled to the benefit of the filing date.

For purposes of the USPTO extra-statutory requirements, the present application constitutes a continuation-in-part of U.S. patent application Ser. No. 12/378,152, entitled SYSTEMS CONFIGURED TO POWER AT LEAST ONE DEVICE DISPOSED IN A LIVING SUBJECT, AND RELATED APPARATUSES AND METHODS, naming RODERICK A. HYDE, MURIEL Y. ISHIKAWA, DENNIS J. RIVET, LOWELL L. WOOD, JR., AND VICTORIA Y. H. WOOD as inventors, filed 11 Feb. 2009 now U.S. Pat. No. 8,295,941, or is an application of which a currently application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

All subject matter of the Related Applications and of any and all parent, grandparent, great-grandparent, etc. applications of the Related Applications is incorporated herein by reference to the extent such subject matter is not inconsistent herewith.

SUMMARY

In an embodiment, a system includes an electrical-power source configured to be disposed within a living subject and provide electrical energy. The system further includes an internal power transmitter configured to be disposed within the living subject, and coupled to the electrical power source to receive at least a portion of the electrical energy therefrom. The internal power transmitter may be further configured to deliver energy out of the living subject, with the energy having a power of at least about 10 µW, in response to receiving the at least a portion of the electrical energy.

In an embodiment, a method includes storing electrical energy in an energy-storage device disposed within a living subject. The method further includes, in response to an internal power transmitter receiving at least a portion of the electrical energy, delivering energy out of the living subject from the internal power transmitter to an external device located external to the living subject, with the energy having a power of at least about 10 µW.

In an embodiment, a method includes receiving energy delivered out of a living subject from an internal power transmitter disposed therein. The method further includes powering at least one device located external to the living subject using the energy.

In an embodiment, a method includes receiving energy delivered out of a living subject from an internal power transmitter disposed therein. The method further includes storing at least a portion of the energy in a first device located external to the living subject.

In an embodiment, a system includes an electricity generator configured to convert internal body energy of a living subject to electrical energy. The system further includes an internal power transmitter configured to be disposed in the living subject. The internal power transmitter operably coupled to the electricity generator to receive at least a portion of the electrical energy therefrom. The internal power transmitter may be further configured to deliver energy out of the living subject in response to receiving the at least a portion of the electrical energy.

In an embodiment, a method includes generating electrical energy internally within a living subject. The method further includes, in response to receiving at least a portion of the electrical energy, delivering energy out of the living subject from an internal power transmitter to an external device.

In an embodiment, an apparatus configured for disposal in a living subject is disclosed. The apparatus includes an electrical-power source configured to provide electrical energy and an internal power transmitter coupled to the electrical power source to receive at least a portion of the electrical energy therefrom. The internal power transmitter is configured to deliver energy out of the living subject in response to receiving at least a portion of the electrical energy, with the energy having a power of at least about 10 µW. A biocompatible protective packaging at least partially encloses the electrical-power source and the internal power transmitter.

In an embodiment, an apparatus configured for disposal in a living subject is disclosed. The apparatus includes an electricity generator configured to convert internal body energy of the living subject to electrical energy, and an internal power transmitter configured to deliver energy out of the living subject in response to receiving at least a portion of the electrical energy. A biocompatible protective packaging at least partially encloses the electricity generator and the internal power transmitter.

The foregoing is a summary and thus may contain simplifications, generalizations, inclusions, and/or omissions of detail; consequently, the reader will appreciate that the summary is illustrative only and is NOT intended to be in any way limiting. Other aspects, features, and advantages of the devices and/or processes and/or other subject matter described herein will become apparent after reading the teachings set forth herein.

BRIEF DESCRIPTION OF THE FIGURES

FIG. 1A is a functional block diagram of an embodiment of a system configured to deliver energy transdermally out of a living subject for powering at least one external device.

FIG. 1B is a functional block diagram of an embodiment of a system configured to deliver energy transdermally out of a living subject for powering at least one external device.

FIG. 2 is a functional block diagram of an embodiment of a system configured to deliver optical power out of a living subject through a portal formed therein.

FIG. 3 is a functional block diagram of an embodiment of a system configured to deliver electrical power out of a living subject through a portal formed therein.

DETAILED DESCRIPTION

Figure 1C:
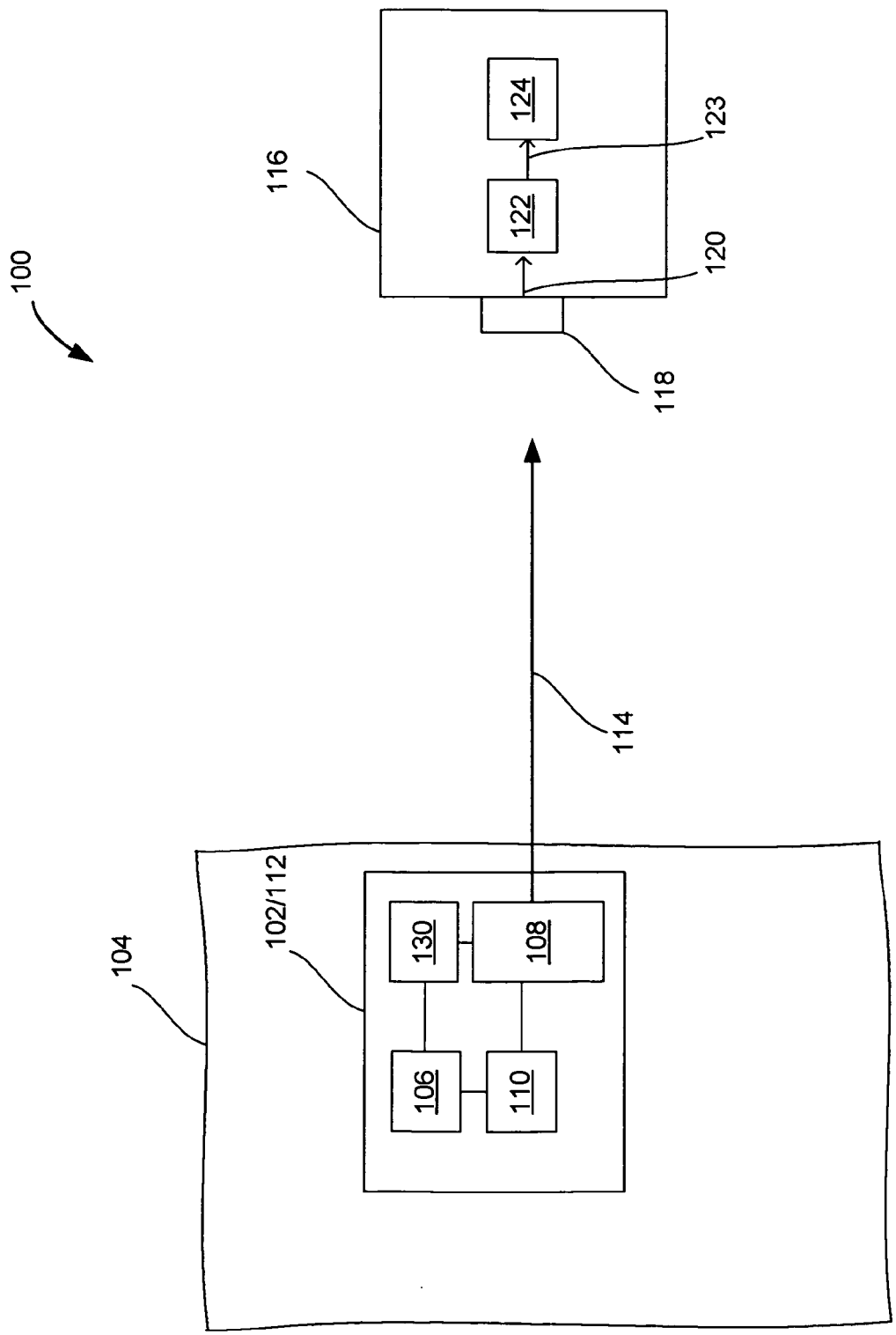
FIG. 1C is a functional block diagram of the system shown in FIG. 1A, with a power converter coupled between the internal power transmitter and the electrical-power source according to an embodiment.

Embodiments disclosed herein are directed to systems configured to deliver energy out of a living subject to power at least one external device, and related apparatuses and methods of use. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein.

FIG. 1A is a functional block diagram of an embodiment of a system 100 configured to deliver energy transdermally out of a living subject for powering at least one external device. The system 100 includes an apparatus 102 configured to be disposed within a living subject 104, such as being embedded in tissue, muscle, or bone of a human being. The apparatus 102 includes an electrical-power source 106, an internal power transmitter 108 operably coupled to the electrical-power source 106 to receive electrical power (e.g., one or more electrical signals) therefrom, and control electrical circuitry 110 configured to control distribution of the electrical power from the electrical-power source 106 to the internal power transmitter 108 and the operation of the internal power transmitter 108. The internal power transmitter 108 is configured to convert at least a portion of the electrical power received from the electrical-power source 106 into a different type of energy 114 and deliver the energy 114 transdermally through and out of tissue of the living subject 104 at a power of, for example, at least about 10 µW.

The electrical-power source 106, internal power transmitter 108, and control electrical circuitry 110 may be configured to be disposed in the living subject 104, such as by being sized for being disposed in the living subject 104 or being biocompatible with the living subject 104. For example, the electrical-power source 106, internal power transmitter 108, and control electrical circuitry 110 may be compactly enclosed in a biocompatible protective packaging 112 that is disposed within the living subject 104 to form the apparatus 102. In an embodiment, the electrical-power source 106, internal power transmitter 108, and control electrical circuitry 110 may each be individually enclosed in separate biocompatible protective packaging sections.

The system 100 further includes at least one external device 116 positioned or positionable externally to the living subject 104 to receive the converted energy 114 transmitted out of the living subject 104. For example, the external device 116 may include an electronic device, such as a cell phone, personal data assistant, a video game device, a therapeutic device, a sensor, or an electronic medical device (e.g., a hearing aid). The external device 116 includes a converter 118 configured to convert the received energy 114 into electrical power 120. For example, the converter 118 may be integrated with or separate from the external device 116. The external device 116 may further include an energy-storage device 122 (e.g., a capacitive device or a battery) configured to store the converted electrical power 120 for powering the external device 116, and control electrical circuitry 124 operably coupled to the energy-storage device 122 and configured to control the distribution of one or more electrical power signals 123 from the energy-storage device 122 and the operation of the external device 116.

In operation, the electrical-power source 106 provides the internal power transmitter 108 with the electrical power, and the internal power transmitter 108 converts at least a portion of the electrical power into the energy 114, which is transmitted transdermally out of the living subject 104 with, for example, a power of at least about 10 µW. More specifically, the internal power transmitter 108 transmits the energy 114 transdermally through and out of the living subject 104 in response to instructions from the control electrical circuitry 110, which is received by the converter 118 of the external device 116. In an embodiment, the control electrical circuitry 110 may be pre-programmed to direct the internal power transmitter 108 to output the energy 114 at specific times throughout the day. In an embodiment, the control electrical circuitry 110 may include or be associated with a data receiver (e.g., an optical or radio-frequency receiver) configured to receive instructions from an external device transmitted transdermally thereto, and the control electrical circuitry 110 may control the operation of the internal power transmitter 108 in response thereto. The energy 114 may be received by the converter 118, which converts the received energy 114 to the electrical power 120. The electrical power 120 may be stored in the energy-storage device 122 and used to power the external device 116. For example, the control electrical circuitry 124 receives the one or more electrical power signals 123 from the energy-storage device 122 to power and control the operation of the external device 116.

In an embodiment, the converter 118 of the external device 116 may be placed in proximity to the internal power transmitter 108 and abut tissue of the living subject 104. In an embodiment, the power of the energy 114 transdermally output from the internal power transmitter 108 may be sufficient so that the external device 116 may be positioned remote from the living subject 104 and the internal power transmitter 108 disposed therein.

The internal power transmitter 108 may receive power from a variety of different types of power sources. According to one or more embodiments, the electrical-power source 106 may include an energy storage device, such as a battery or a capacitive device. For example, referring to FIG. 1B, in an embodiment, the electrical-power source 106 may include an electricity generator 126 configured to convert internal body energy of the living subject 104 to electrical energy. For example, the electricity generator may include at least one of a fluid-flow generator configured to convert internal body fluid motion into electricity, a fluid-pressure generator configured to convert internal fluid pressure into electricity, a muscle-motion generator configured to convert internal muscle motion into electricity, an acceleration-motion generator configured to convert acceleration of the living subject 104 into electricity, or a thermal-electric generator configured to convert internal body heat into electricity. The electrical-power source 106 may further include an energy-storage device 128 (e.g., a battery or capacitive device) coupled to the electricity generator 126 and configured to store electrical energy generated thereby. In such an embodiment, the control electrical circuitry 110 may be operably coupled to the energy-storage device 128 and control distribution of the electricity therefrom to the internal power transmitter 108. In an embodiment, the electricity generator 126 may be omitted, and the energy-storage device 128 may be a disposable or re-chargeable battery that powers the internal power transmitter 108. In some embodiments, the energy-storage device 126 and the electricity generator 128 may be separately packaged in a biocompatible packaging.

The internal power transmitter 108 may be configured to deliver the energy 114 out of the living subject 104 with, for example, a power of at least about 10 µW. In more specific embodiments, the power output by the internal power transmitter 108 may range from about 10 µW to about 10 W, about 10 µW to about 1 mW, about 1 mW to about 100 W, about 100 mW to about 1 W, about 1 W to about 5 W, about 5 W to about 10 W, about 10 µW to about 100 W, about 1 W to about 100 W, or about 20 W to about 100 W. The internal power transmitter 108 may output the energy 114 at a selected one or more wavelengths that are transmittable through tissue of the living subject 104. For example, the selected one or more wavelengths may include one or more infrared wavelengths having a wavelength of about 800 nm to about 1 mm. The selected one or more wavelengths may include one or more visible wavelengths having a wavelength of about 380 nm to about 750 nm. The control electrical circuitry 110 may be configured to direct the internal power transmitter 108 to output the energy 114 with one or more selected optical parameters. For example, the one or more selected optical parameters may include wavelength, start time, duration, end time, power, or time-integrated power of the one or more optical power signals 110.

The internal power transmitter 108 may be chosen from a number of different types of transducers that are configured to convert electrical energy to another form of energy. In an embodiment, the transducer may include an electrical-optical converter configured to convert at least a portion of the electrical power received from the electrical-power source 106, and deliver the converted electrical power as the energy 114 in the form of electromagnetic energy such as one or more optical power signals. For example, the electrical-optical converter may be a light-emitting device, such as one or more light-emitting diodes or one or more laser diodes. In such an embodiment, the converter 118 of the external device 116 may be an optical-electrical converter (e.g., one or more photodiodes) configured to convert the received energy 114 to the electrical power 120.

In an embodiment, the transducer may include an electrical-magnetic converter configured to convert at least a portion of the electrical power received from the electrical-power source 106, and output the converted electrical power as the energy 114 in the form of magnetic energy. For example, the electrical-magnetic converter may be an electromagnet. In such an embodiment, the converter 118 of the external device 116 may be an magnetic-electrical converter (e.g., induction coil) configured to convert the received energy 114 to the electrical power 120.

In an embodiment, the transducer may include one or more ultrasonic elements configured to convert at least a portion of the electrical power received from the electrical-power source 106, and output the converted electrical power as the energy 114 in the form of ultrasonic energy. For example, the one or more ultrasonic elements may be one or more piezoelectric elements. In such an embodiment, the converter 118 of the external device 116 may also include one or more ultrasonic elements configured to convert the received ultrasonic energy to the electrical power 120.

In an embodiment, the transducer may include a heating element configured to convert at least a portion of the electrical power received from the electrical-power source 106 to the energy 114 in the form of thermal energy. For example, the heating element may be one or more resistance heating elements. In such an embodiment, the converter 118 of the external device 116 may also include a thermal-electric converter (e.g., one or more Peltier cells or an alkali metal thermal-electric converter) configured to convert the received ultrasonic energy to the electrical power 120.

In an embodiment, the transducer may include a radio-frequency device configured to convert at least a portion of the electrical power received from the electrical-power source 106 to the energy 114 in the form of radio-frequency energy. For example, the radio-frequency device may be a radio-frequency transmitter. In such an embodiment, the converter 118 of the external device 116 may include a radio-frequency receiver configured to convert the received radio-frequency energy to the electrical power 120.

As previously discussed, the electrical-power source 106 and components thereof, the internal power transmitter 108, and the control electrical circuitry 110 may be enclosed in the biocompatible protective packaging 112 that is at least partially transparent to the energy 114 output by the internal power transmitter 108. The biocompatible protective packaging 112 may be formed from a number of different biocompatible polymeric materials, such as at least one of polyxylene, polyethylene, poly(ethylene oxide), polyurethane, or poly(butylene terephthalate). The biocompatible protective packaging 112 may also be formed from a number of different biocompatible ceramics, such as silicate-based ceramics. In some embodiments, the biocompatible protective packaging 112 may be in the form of a biocompatible coating made from at least one of the aforementioned biocompatible polymeric on ceramic materials and formed over a relatively less biocompatible housing that provides structural support for the biocompatible coating or a housing formed from at least one of the aforementioned biocompatible materials.

According to one or more embodiments of an operational method when the electrical-power source 106 includes an energy-storage device, electrical energy may be stored in the energy-storage device. In response to the internal power transmitter 108 receiving at least a portion of the stored electrical energy, the internal power transmitter 108 may deliver energy out of the living subject at any of the disclosed power levels or ranges.

In an embodiment, the electrical energy may be generated internally within the living subject 104 using any of the disclosed electricity generators 126 (FIG. 1B) configured to convert internal body energy of the living subject 104 to electrical energy. In response to the internal power transmitter 108 receiving at least a portion of the internally generated electrical energy, the internal power transmitter 108 may deliver energy out of the living subject at any of the disclosed power levels or ranges. In an embodiment, the internally generated electrical energy may stored in the energy-storage device 128 (FIG. 1B) prior to being supplied to the internal power transmitter 108 and delivered out of the living subject 104.

From another perspective, according to one or more embodiments of an operational method, the external device 116 may receive the energy 114 delivered out of the living subject 104 from the internal power transmitter 108. The external device 116 may be powered using the received energy 114.

Referring to FIG. 1C, in an embodiment, a power converter 130 may be coupled between the internal power transmitter 108 and the electrical-power source 106. The power converter 130 is configured to selectively condition received electrical power from the electrical-power source 106 to generate one or more conditioned electrical power signals, under the control of the control electrical circuitry 110, for powering the internal power transmitter 108. For example, the power converter 130 may be configured to convert electrical power from the electrical-power source 106 from a first format to a second format, such as from a DC waveform to an AC waveform, an AC waveform to a DC waveform, a DC waveform to a different DC waveform, or an AC waveform to a different AC waveform.

Referring to FIG. 2, in one or more embodiments, the energy 114 output by the internal power transmitter 108 may be delivered out of the living subject 104 through a portal. FIG. 2 is a functional block diagram of an embodiment of a system 200 configured to deliver optical power through a portal formed in the living subject. In the system 200, the internal power transmitter 108 is configured as an electrical-optical converter that outputs the energy 114 as one or more optical power signals. An optical waveguide 202 (e.g., one or more optical fibers) may be optically coupled to the electrical-optical converter to receive the energy 114 output therefrom and guide the energy 114 to a selected location in or out of the living subject 104. The optical waveguide 202 may extend out of the living subject 104 through a trocar housing 204 disposed in the living subject 104 that defines a portal therein.

In operation, the optical waveguide 202 may output the energy 114 as a beam that is received by the converter 118 of the external device 116. In an embodiment, the optical waveguide 202 may be optically coupled to the converter 118 using a suitable optical connector structure or optical outlet received at least partially by the trocar housing 204. However, in another embodiment, the energy 114 may travel through free space to the converter 118 along with, optionally, being focused by one or more optical elements (e.g., one or more lenses) or directed to the converter 118.

Referring to FIG. 3, in one or more embodiments, electrical energy may be delivered out of the living subject 104 through a portal, such as an electrical outlet, to power at least one external device. FIG. 3 is a functional block diagram of an embodiment of a system 300 configured to deliver electrical power through an electrical outlet disposed in a living subject. The system 300 includes an apparatus 302 configured to be disposed within the living subject 104, such as being embedded in tissue, muscle, or bone of a human being. The apparatus 302 may include an electricity generator 304 configured to convert internal body energy of the living subject 104 to electrical energy. For example, the electricity generator may include at least one of a fluid-flow generator configured to convert internal body fluid motion into electricity, a fluid-pressure generator configured to convert internal fluid pressure into electricity, a muscle-motion generator configured to convert internal muscle motion into electricity, an acceleration-motion generator configured to convert acceleration of the living subject 104 into electricity, or a thermal-electric generator configured to convert internal body heat into electricity. The apparatus 302 may further include an energy-storage device 306 (e.g., a battery or capacitive device) coupled to the electricity generator 304 to receive and store electrical power generated thereby. Control electrical circuitry 308 may be operably coupled to the energy-storage device 306 and control distribution of the electrical power. The electricity generator 304, energy-storage device 306, and control electrical circuitry 308 may be individually or collectively enclosed in a biocompatible packaging 309 that is the same or similar to the biocompatible packaging 112 shown in FIG. 1A.

The apparatus 302 may further include one or more electrical conductors 310 (e.g., one or more electrical wires) electrically coupled to the energy-storage device 306 and suitably protected by a biocompatible sheath. The one or more electrical conductors 310 may extend through a trocar housing 312 disposed in the living subject 104 that defines a portal therein. An electrical interface 314 (e.g., an electrical outlet) is electrically coupled to the one or more electrical conductors 310 and may be disposed in or project outwardly from the trocar housing 312 and the living subject 104. One or more electrical power signals may be transmitted from the energy-storage device 306, through the one or more electrical conductors 310, and to the electrical interface 314.

The system 300 further includes at least one external device 316 positioned or positionable externally to the living subject 104 to receive the electrical power from the electrical outlet 314. For example, the external device 316 may include a electronic device, such as a cell phone, personal data assistant, a video game device, a therapeutic device, a sensor, or an electronic medical device (e.g., a hearing aid). The external device 316 includes an electrical interface 318 (e.g., an electrical plug) configured to interface with the electrical interface 314 so that the stored electrical power can be delivered out of the living subject 104 to an energy-storage device 320 (e.g., a capacitive device or a battery) of the external device 316. The external device 316 further includes control electrical circuitry 322 operably coupled to the energy-storage device 320 and configured to control the distribution of electrical power 324 from and stored in the energy-storage device 320.

In operation, the electrical power may be delivered from energy-storage device 306 through the electrical interface 314, to the electrical interface 318, and to the energy-storage device 320.

In some embodiments, the electricity generator 304 may be omitted, and the energy-storage device 306 may be configured as a battery that provides the electrical power to the external device 316. Furthermore, in an embodiment, the control electrical circuitry 322 may include a power converter that is configured to convert the electrical power from a first format to a second format. For example, the power converter may be configured to convert the electrical power from a direct-current waveform to an alternating-current waveform.

Figure 4:
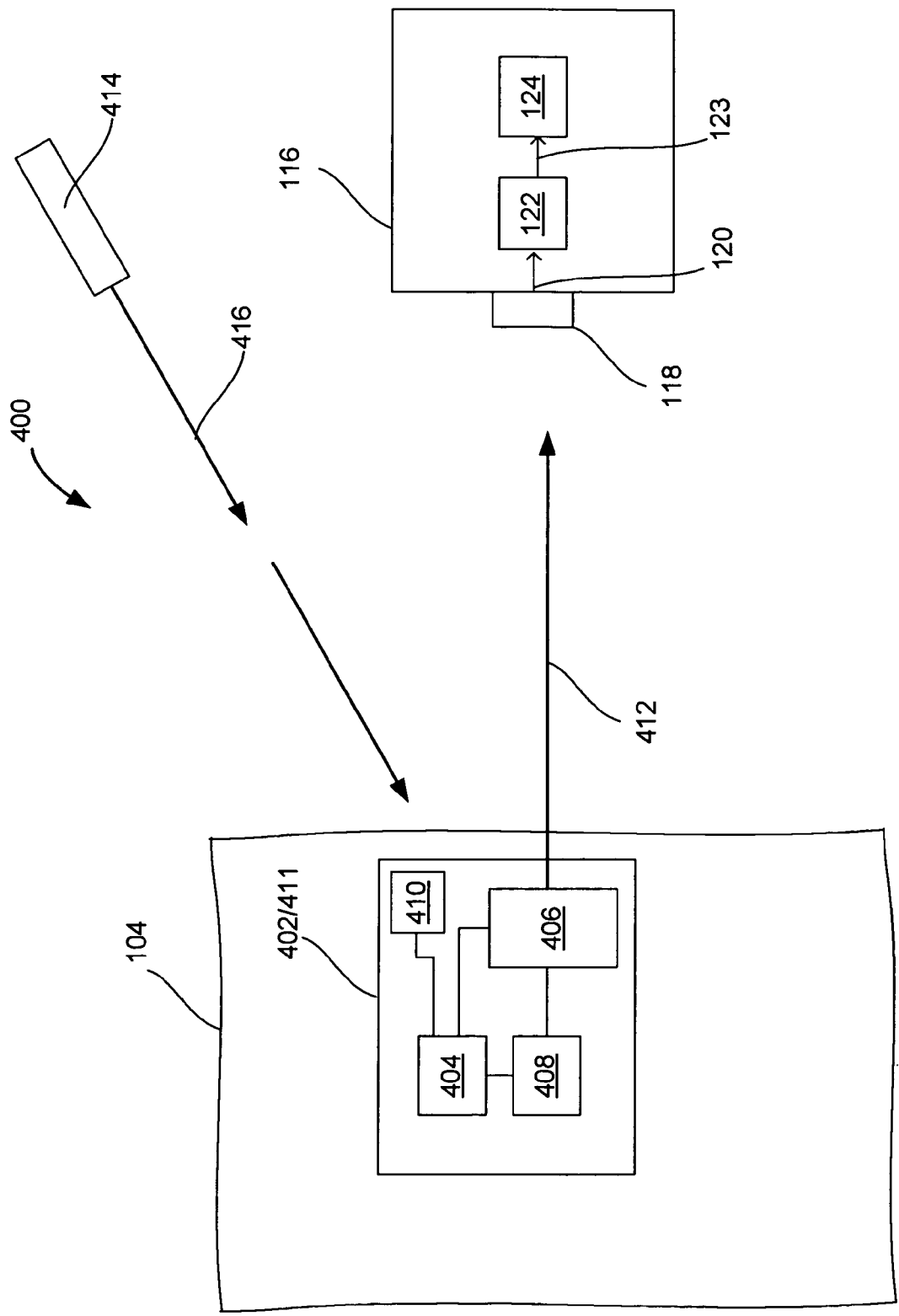
FIG. 4 is a functional block diagram of an embodiment of a system configured so that an energy-storage device disposed in a living subject may be re-charged according to an embodiment.

FIG. 4 is a functional block diagram of an embodiment of a system 400 configured so that an energy-storage device disposed in a living subject may be re-charged. The system 400 includes an apparatus 402 configured to be disposed within a living subject 104, such as being embedded in tissue, muscle, or bone of a human being. The apparatus 402 includes an energy-storage device 404 (e.g., a battery or a capacitive device), an internal power transmitter in the form, for example, of an internal power transmitter 406 (e.g., electrical-optical converter or any other disclosed internal power transmitter) operably coupled to the energy-storage device 404 to receive electrical power (e.g., one or more electrical signals) therefrom, and control electrical circuitry 408 configured to control distribution of the electrical power from the energy-storage device 404 to the internal power transmitter 406 and the operation of the internal power transmitter 406. The internal power transmitter 406 is configured to convert at least a portion of the electrical power received from the energy-storage device 404 into energy 412 that is transdermally transmittable through and out of tissue of the living subject 104 at a power of, for example, at least about 10 µW or any other disposed power level or range. The apparatus 402 further includes an optical-electrical converter 410 configured to receive and convert optical energy to electrical power 412. The energy-storage device 404 is coupled to the optical-electrical converter to receive the electrical power 412 therefrom in order to re-charge the energy-storage device 404. The energy-storage device 404, internal power transmitter 406, control electrical circuitry 408, and optical-electrical converter 410 may be individually or collectively enclosed in a biocompatible packaging 411 that is the same or similar to the biocompatible packaging 112 shown in FIG. 1A.

The system 400 further includes an optical power source 414 configured to output electromagnetic energy 416 as, for example, a beam of electromagnetic energy that is transdermally transmittable into the living subject 104.

In operation, the optical power source 414 outputs the electromagnetic energy 416, which is transmitted transdermally into the living subject 104. The transdermally transmitted electromagnetic energy 416 is received by the optical-electrical converter 410, which converts at least a portion thereof to the electrical power that re-charges the energy-storage device 404. The re-charged energy-storage device 404 may deliver electrical power to the internal power transmitter 406, which converts at least a portion of the electrical power received therefrom to the energy 412 for powering the external device 116. The powering and operation of the external device 116 using the energy 412 has been previously described and is not repeated in the interest of brevity.

However, it is noted that other types of power receivers and converters may be employed besides the illustrated optical-electrical converter 410. For example, the energy-storage device 404 may include or be otherwise associated with a power receiver configured to receive power transmitted transdermally into the living subject 104 and a power converter operably coupled to the power receiver to convert the received power to electrical power. For example, the power receiver and the power converter may form an integrated device such as an inductive receiver/converter.

Figure 5:
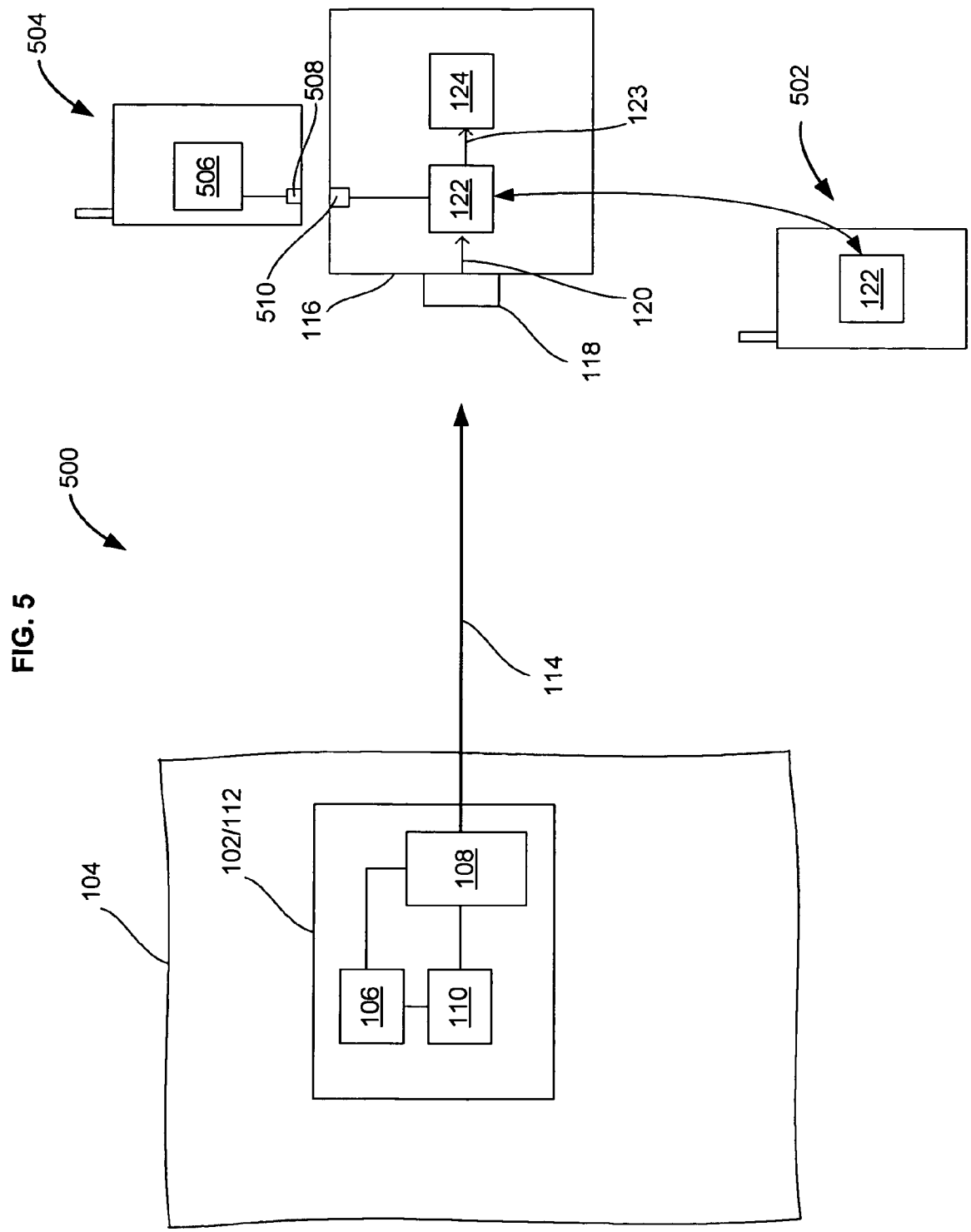
FIG. 5 is a functional block diagram of an embodiment of a system in which power stored in a first external device received from an internal power transmitter may be supplied to another external device.

Referring to the functional block diagram shown in FIG. 5 depicting an embodiment of a system 500, electrical power stored by a first external device may be supplied to one or more other external devices. In an embodiment, the energy-storage device 122 of the external device 116 may be a removable battery. In use, the energy-storage device 122 may be removed from the external device 116 and installed in a second external device 502 (e.g., cell phone, a hearing aid, a personal data assistant, a therapeutic device, a sensor, or other electronic device) to power the second external device 502.

In an embodiment, an external device 504 (e.g., cell phone, a therapeutic device, a sensor, a personal data assistant, or other electronic device) may include control electrical circuitry 506 configured to control the operation thereof and a power interface 508 coupled to the control electrical circuitry 506 for supplying power to the control electrical circuitry 506. For example, the power interface 508 may include an inductive receiver, an electrical receiver (e.g., electrical socket coupled to the control electrical circuitry 506), or other suitable interface configured to receive power from another device and transmit such received power to the control electrical circuitry 506. In such an embodiment, the external device 116 may be provided with a power interface 510 configured to transmit power from the energy-storage device 122 to the control electrical circuitry 506. For example, the power interface 510 may be an inductive transmitter that inductively couples power to the power interface 508 when it is configured as an inductive receiver, an electrical plug that electrically couples to the power interface 508 when it is an electrical socket, or other suitable power interface configured to transfer power between the energy-storage device 122 and the control electrical circuitry 506.

It is noted that while the system 500 is illustrated as employing the apparatus 102 for providing the energy 114 to the external device 116, any of the disclosed internal apparatuses configured to deliver energy out of the living subject may be employed in the system 500. For example, the apparatus 102 may be replaced with the apparatus 302 provided the external device 116 is provided with a suitable electrical interface to transfer power to the energy-storage device 122 thereof.

The reader will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. The reader will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. The reader will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein may be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components may be referred to herein as "configured to." The reader will recognize that "configured to" can generally encompass active-state components and/or inactive-state components and/or standby-state components, etc. unless context requires otherwise.

In some instances, one or more components may be referred to herein as "configured to." The reader will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, the recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

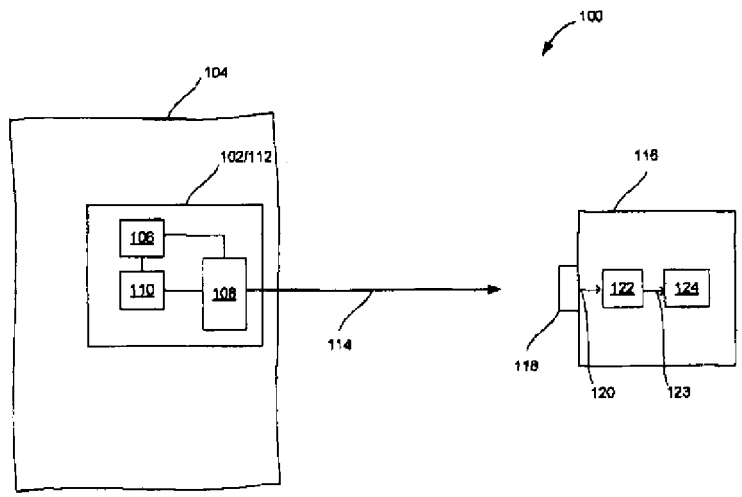

The invention claimed is:

1. A system, comprising:
   an electricity generator configured to convert internal body energy of a living subject to electrical energy; and
   an internal power transmitter configured to be disposed in the living subject, the internal power transmitter operably coupled to the electricity generator to receive at least a portion of the electrical energy therefrom, the internal power transmitter includes a transducer configured to convert the at least a portion of the electrical energy to a second type of energy, the internal power transmitter further configured to deliver the second type of energy out of the living subject.

2. The system of claim 1, wherein the electricity generator includes at least one of fluid-flow generator, a fluid-pressure generator, a muscle-motion generator, an acceleration-motion generator, or a thermal-electric generator.

3. The system of claim 1, further comprising an energy-storage device configured to store the electrical energy generated by the electricity generator, the internal power transmitter coupled to the energy-storage device to receive the at least a portion of the electrical energy therefrom.

4. The system of claim 3, wherein the energy-storage device includes a battery.

5. The system of claim 1, wherein the second type of energy is transdermally transmittable out of the living subject.

6. The system of claim 1, wherein the internal power transmitter includes an electrical-optical converter configured to output the second type of energy as one or more optical power signals.

7. The system of claim 1, wherein the internal power transmitter includes a converter configured to output the second type of energy as electromagnetic energy.

8. The system of claim 1, wherein the internal power transmitter includes an electrical-magnetic converter configured to output the second type of energy as magnetic energy.

9. The system of claim 1, wherein the internal power transmitter includes one or more ultrasonic elements configured to output the second type of energy as ultrasonic energy.

10. The system of claim 1, wherein the internal power transmitter includes a heating element configured to output the second type of energy as thermal energy.

11. The system of claim 1, wherein the internal power transmitter includes a radio-frequency device configured to output the second type of energy as radio-frequency energy.

12. The system of claim 1, wherein the internal power transmitter includes one or more electrical conductors configured to transmit the energy therethrough as an electrical current.

13. The system of claim 1, wherein the internal power transmitter is configured to output the second type of energy such that the second type of energy is transdermally transmittable out of the living subject.

14. The system of claim 1, further comprising an external device positionable to receive at least a portion of the second type of energy from the internal power transmitter and configured to be powered by the at least a portion of the second type of energy.

15. The system of claim 14, wherein the external device is configured to convert the received at least a portion of the second type of energy to one or more electrical power signals to power the external device.

16. The system of claim 14, wherein the external device includes at least one of a hearing aid, a cellular phone, a therapeutic device, a sensor, or a personal data assistant.

17. The system of claim 1, further comprising an external device positionable to receive at least a portion of the second type of energy from the internal power transmitter and configured to store the at least a portion of the second type of energy.

18. The system of claim 1, further comprising a power converter configured to convert the electrical energy from a first format to a second format.

19. The system of claim 1, wherein the internal power transmitter is configured to output the energy with the power at about 1 W to about 100 W.

20. A method, comprising:
generating electrical energy internally within a living subject with an electricity generator;
converting at least a portion of the electrical energy to a second type of energy with a transducer; and
delivering the second type of energy out of the living subject from an internal power transmitter to charge or power an external device.

21. The method of claim 20, wherein the electricity generator includes at least one of a fluid-flow generator, a fluid-pressure generator, a muscle-motion generator, an acceleration-motion generator, or a thermal-electric generator.

22. The method of claim 20, further comprising storing the electrical energy in an energy-storage device disposed within the living subject.

23. The method of claim 20, wherein the second type of energy includes at least one of one or more optical signals, electromagnetic energy, magnetic energy, ultrasonic energy, thermal energy, or radio-frequency energy.

24. The method of claim 20, wherein delivering the second type of energy out of the living subject from an internal power transmitter to an external device includes transdermally transmitting the second type of energy out of the living subject.

25. The method of claim 20, wherein delivering the second type of energy out of the living subject from an internal power transmitter to an external device includes transmitting the second type of energy through a portal disposed in the living subject.

26. The method of claim 25, wherein transmitting the second type of energy through a portal disposed in the living subject includes transmitting one or more optical signals through an optical portal.

27. The method of claim 25, wherein transmitting the second type of energy through a portal disposed in the living subject includes transmitting one or more electrical power signals through the portal.

28. The method of claim 20, wherein the power is about 100 mW to about 1 W.

29. The method of claim 20, wherein the power is about 1 W to about 100 W.

30. A method, comprising:
generating electrical energy internally within a living subject with an electrical generator;
converting at least a portion of the electrical energy to a second type of energy with a transducer;
delivering the second type of energy out of the living subject from an internal power transmitter;
converting the second type of energy to electrical power;
powering at least one device located externally to the living subject using the electrical power; and
utilizing the powering to control an operation of the at least one device.

31. The method of claim 30, wherein the electricity generator includes at least one of a fluid-flow generator, a fluid-pressure generator, a muscle-motion generator, an acceleration-motion generator, or a thermal-electric generator.

32. The method of claim 30, wherein the second type of energy includes at least one of one or more optical signals, electromagnetic energy, magnetic energy, ultrasonic energy, thermal energy, or radio-frequency energy.

* * * * *

UNITED STATES PATENT AND TRADEMARK OFFICE
CERTIFICATE OF CORRECTION

PATENT NO.       : 8,463,391 B2  
APPLICATION NO.  : 12/456846  
DATED            : June 11, 2013  
INVENTOR(S)      : Hyde et al.

Page 1 of 2

It is certified that error appears in the above-identified patent and that said Letters Patent is hereby corrected as shown below:

Delete title page and substitute therefore the attached title page showing the corrected number of claims in patent.

IN THE CLAIMS:

Column 15, lines 4-7 cancel claim 12.

Column 16, lines 19-22 cancel claim 27.

Signed and Sealed this  
Thirteenth Day of May, 2014

Michelle K. Lee  
*Deputy Director of the United States Patent and Trademark Office*

(12) United States Patent
Hyde et al.

(10) Patent No.: US 8,463,391 B2
(45) Date of Patent: *Jun. 11, 2013

(54) SYSTEMS CONFIGURED TO DELIVER ENERGY OUT OF A LIVING SUBJECT, AND RELATED APPARTUSES AND METHODS

(75) Inventors: Roderick A. Hyde, Redmond, WA (US); Muriel Y. Ishikawa, Livermore, CA (US); Jordin T. Kare, Seattle, WA (US); Dennis J. Rivet, Portsmouth, VA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 803 days.

This patent is subject to a terminal disclaimer.

(21) Appl. No.: 12/456,846

(22) Filed: Jun. 23, 2009

(65) Prior Publication Data

US 2010/0065097 A1 Mar. 18, 2010

Related U.S. Application Data

(63) Continuation-in-part of application No. 12/378,152, filed on Feb. 11, 2009, now Pat. No. 8,295,941, and a continuation-in-part of application No. 12/316,811, filed on Dec. 15, 2008, now Pat. No. 8,280,520, and a continuation-in-part of application No. 12/283,911, filed on Sep. 15, 2008, now Pat. No. 8,340,777.

(51) Int. Cl.
*A61N 1/00* (2006.01)

(52) U.S. Cl.
USPC .............................. 607/60; 607/61

(58) Field of Classification Search
USPC .............................. 607/60, 61
See application file for complete search history.

(56) References Cited

U.S. PATENT DOCUMENTS

| | | |
|---|---|---|
| 5,320,098 A | 6/1994 | Davidson |
| 5,387,259 A * | 2/1995 | Davidson .................... 600/310 |
| 5,835,457 A | 11/1998 | Nakajima |
| 5,889,735 A | 3/1999 | Kawata et al. |
| 5,897,330 A | 4/1999 | Watanabe et al. |
| 6,898,464 B2 | 5/2005 | Edell et al. |
| 2006/0139000 A1 * | 6/2006 | Bailey et al. ............... 320/114 |
| 2007/0027505 A1 | 2/2007 | Ginggen |
| 2008/0097545 A1 | 4/2008 | Propato |
| 2009/0171404 A1 * | 7/2009 | Irani et al. ............. 607/2 |

OTHER PUBLICATIONS

Roderick A. Hyde et al., U.S. Appl. No. 12/283,911, filed Sep. 15, 2008, "Systems Configured to Transmit Optical Power Signals Transdermally Out of a Living Subject, and Devices and Methods".
Roderick A. Hyde et al., U.S. Appl. No. 12/316,811, filed Dec. 15, 2008, "Systems Configured to Locate a Photonic Device Disposed in a Living Subject, and Related Apparatuses and Methods".
Roderick A. Hyde et al., U.S. Appl. No. 12/378,152, filed Feb. 11, 2009, "Systems Configured to Power At Least One Device Disposed in a Living Subject, and Related Apparatuses and Methods".
U.S. Appl. No. 13/604,005, filed Oct. 29, 2012, Hyde et al.
U.S. Appl. No. 13/603,904, filed Oct. 29, 2012, Hyde et al.
U.S. Appl. No. 13/603,859, filed Oct. 29, 2012, Hyde et al.

* cited by examiner

*Primary Examiner* — Eric D. Bertram
(74) *Attorney, Agent, or Firm* — Workman Nydegger

(57) ABSTRACT

Embodiments disclosed herein are directed to systems configured to deliver energy out of a living subject to power at least one external device, and related apparatuses, and methods of use.

30 Claims, 7 Drawing Sheets